(12) United States Patent
Takeuchi et al.

(10) Patent No.: US 7,038,768 B2
(45) Date of Patent: May 2, 2006

(54) OPTICAL MEASURING METHOD FOR SEMICONDUCTOR MULTIPLE LAYER STRUCTURES AND APPARATUS THEREFOR

(75) Inventors: Hideo Takeuchi, Tokyo (JP);
Yoshitsugu Yamamoto, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 336 days.

(21) Appl. No.: 10/642,184

(22) Filed: Aug. 18, 2003

(65) Prior Publication Data
US 2005/0099623 A1 May 12, 2005

(30) Foreign Application Priority Data
Jan. 17, 2003 (JP) ............... 2003-009515

(51) Int. Cl.
*G01J 3/00* (2006.01)
*G01J 3/08* (2006.01)
*G01J 3/28* (2006.01)

(52) U.S. Cl. .................. 356/73; 356/317; 356/318; 356/432; 356/445

(58) Field of Classification Search ............ 356/73, 356/317, 318, 432
See application file for complete search history.

(56) References Cited

U.S. PATENT DOCUMENTS
5,064,283 A * 11/1991 Tober .................. 356/73

FOREIGN PATENT DOCUMENTS
JP 11-51856 2/1999
JP 2001-110806 4/2001

OTHER PUBLICATIONS
H. Shen et al., "Franz-Keldysh Oscillations In Modulation Spectroscopy", *J. Appl. Phys.*, Aug. 1995, pp. 2151-2176, 78(4).
T. Katoda, "Techniques For Evaluating a Semiconductor", *Textbook*, 1989.

* cited by examiner

*Primary Examiner*—F. L. Evans
(74) *Attorney, Agent, or Firm*—Leydid, Voit & Mayer, Ltd.

(57) ABSTRACT

In a measuring apparatus for a semiconductor multiple layer structure, a spectrometer disperses light from a sample for measurement of the photoluminescence spectrum or disperses probe light to irradiate the sample for the measurement of the reflection spectrum. A controller makes a guide member guide the white light to the spectrometer and acquire electric signals from a first detector for the measurement of the reflection spectrum, and makes the guide member guide the light from the spectrometer to a second detector to acquire electric signals for the measurement of the photoluminescence spectrum.

5 Claims, 6 Drawing Sheets

OPTICAL MEASURING METHOD FOR SEMICONDUCTOR MULTIPLE LAYER STRUCTURES AND APPARATUS THEREFOR

BACKGROUND OF THE INVENTION

1. Field of the Invention

The present invention relates to quality evaluation and control of semiconductor multiple layer structures.

2. Background Art

An epitaxial wafer having a multiple layer structure is used for fabricating semiconductor devices, and the quality evaluation and control therefor are necessary in order to decrease the number of defectives and to reduce the fabrication cost. Items assessed for quality on an epitaxial wafer include thicknesses and compositions of the multiple layers. The thickness is mainly measured with a technique such as infrared-ray or X-ray interference by using interference of electromagnetic waves, or. ellipsometry (polarization analysis) by using change in the degree of polarization between incident and reflecting lights. On the other hand, the compositions of the layers in an epitaxial wafer are evaluated with band gap energies obtained by spectrum measurement of photoluminescence generated by irradiation of excitation light such as laser beams (for example, Masashi Ozaki, Semiconductor Evaluation Technique, Ch. 7 [in Japanese], ed. Takashi Katouda, Sangyo Tosho, Tokyo, 1989).

There are many items assessed on an epitaxial wafer besides the above-mentioned thickness and composition. One of them is the internal electric field strength, known to depend on the doping concentration and the state at the surface/interface in an epitaxial wafer. Further, the internal electric field strength was recently reported to have a correlation with current gain in a heterojunction bipolar transistor. Therefore, the internal electric field strength is regarded as an important item in quality evaluation on an epitaxial wafer.

The internal electric field strength can be measured with a technique called light modulated reflection spectroscopy or photoreflectance (hereinafter referred also to PR) spectroscopy. In this method, a change in reflectance, $\Delta R/R$, caused by irradiating a sample with external modulated light such as laser light, called pumping light, is measured with light called probe light (detection light). The change in reflectance, $\Delta R/R$, is recorded as a function of wavelength or photon energy of the probe light. In a sample having an internal electric field, the change in reflectance, $\Delta R/R$, exhibits an oscillatory profile called Franz-Keldysh oscillations (for example, refer to "Franz-Keldysh Oscillations in Modulation Spectroscopy", H. Shen and M. Dutta, Journal of Applied Physics, vol. 78, pp. 2151–2176 (1995)). The period of the oscillation is determined by the internal electric field strength. Therefore, the internal electric field can be investigated by analyzing the period of the Franz-Keldysh oscillations. Further, Japanese Patent laid open Publication 11-51856/1999 shows that the photoreflectance from a sample can be detected solely from the integrated intensity thereof, without a spectrometer.

The above-mentioned three items, thickness, band gap energy and internal electric field, are measured with techniques different from each other in the evaluation of the quality of the epitaxial wafer. Therefore, much time and work are needed in order to measure all the three items. Further, the cost is high for providing apparatuses for the three measuring techniques. This leads to a barrier for strict quality control.

SUMMARY OF THE INVENTION

An object of the invention is to simply evaluate internal electric field strength, thickness and band gap energy in a semiconductor multiple layer structure.

In one aspect of the invention, in a measuring apparatus for a semiconductor multiple layer structure, a first light source generates light for exciting a sample of the semiconductor multiple layer film to measure photoluminescence spectra and generates external modulated light to the sample for measurement of reflection spectra. A second light source generates white light for probe light to measure the reflection spectra. A spectrometer disperses light from the sample for the measurement of the photoluminescence spectra or disperses light from the first light source to irradiate the sample for the measurement of the reflection spectra. A first detector for the measurement of the photoluminescence spectra detects light emitted from the spectrometer and converts it to an electrical signal, while a second detector for the measurement of the reflection spectra detects light reflected from the sample irradiated with the probe light dispersed by the spectrometer. A guide member guides the light from the spectrometer to the first detector or guides the white light from the second light source to the second detector. A controller makes the guide member guide the white light from the second light source to the first detector and acquire electric signals from the first detector for the measurement of the reflection spectra and makes the changer guide the light from the spectrometer to the second detector and acquire electric signals from the second detector for the measurement of the photoluminescence spectra.

In another aspect of the invention, in a measuring method for a semiconductor multiple layer structure, a sample of semiconductor multiple layer structure is irradiated with excitation light, and photoluminescence from the sample after transmitting a spectrometer is detected while the spectrometer is swept, and the detected light intensity is recorded as a function of photon energy. White light is entered to the spectrometer to irradiate the sample with monochromatic light emitted from the spectrometer, and the spectrometer is swept while the sample is irradiated with the external modulated light to detect reflection light from the sample, and the detected reflection spectra are recorded as a function of photon energy.

An advantage of the present invention is that the internal electric field strength, the thickness and the band gap energy in a semiconductor multiple layer structure can be measured with one apparatus.

Another advantage of the present invention is that the internal electric field strength, the thickness and the band gap energy in a semiconductor multiple layer structure can be measured nondestructively by measuring both photoreflectance and photoluminescence spectra of the semiconductor multiple layer structure.

BRIEF DESCRIPTION OF THE DRAWINGS

These and other objects and features of the present invention will become clear from the following description taken in conjunction with the preferred embodiments thereof with reference to the accompanying drawings, and in which.

DETAILED DESCRIPTION OF THE PREFERRED EMBODIMENTS

Referring now to the drawings, embodiments of the invention are described below. Previously, the thickness, the band gap energy and the internal electric field in a semiconductor multiple layer structure prepared as an epitaxial wafer or the like were measured with different techniques. Then, it is desirable to measure them nondestructively, simultaneously, precisely and simply. In order to solve this problem, it would be necessary to develop a technique/principle for evaluating two or more quality items based on data obtained by one measuring technique and to provide an apparatus which can evaluate two or more items.

Then, the light modulated reflection (photoreflectance (PR)) spectroscopy used for the evaluation of the internal electric field and the photoluminescence (PL) spectroscopy used for evaluating the band gap energy are paid attention. They belong to technical field of spectroscopy and have common components for measurement. Therefore, it may be possible to provide a single apparatus for measuring light modulated reflection spectra or photoluminescence spectra, or PR and PL spectra may be measured by the single apparatus.

Next, evaluation of thickness is paid attention. Many techniques of prior art evaluation for thickness is performed by analyzing spectra affected by interference due to multiple layer structure. Especially, the line shape of reflection/transmission spectra is sensitive to interference. The above-mentioned PR spectroscopy used for evaluating the internal electric field is one of the light-reflection techniques, and it may also be used for evaluating thickness. However, it is not yet known how to analyze the line shape of PR spectra affected by interference in a multiple layer film, and it is not yet used to evaluate thicknesses in a multiple layer structure.

The invention proposes a spectroscopic measurement method for the internal electric field strength and thickness on the basis of PR spectroscopy in order to achieve simple and simultaneous evaluation of the internal electric field strength, thickness and band gap energy in a semiconductor multiple layer structure in an epitaxial wafer. In this method, the internal electric field strength and the thickness are obtained simultaneously from Franz-Keldysh oscillations of the semiconductor multiple layer structure. Further, a spectrum measuring apparatus is proposed to obtain both PR and PL spectra for precise evaluation based on the spectroscopic technologies. In the evaluation of the internal electric field strength and thickness from PR spectra, it is necessary to use band gap energy as a parameter. Then, as will be described below, the spectrum measuring apparatus uses the same spectrometer. Thus, the band gap energy obtained from PR spectra has no relative error to that obtained from PL spectra principally. Then, the apparatus is very advantageous for precise evaluation of thickness based on PR spectra.

Figure 1:
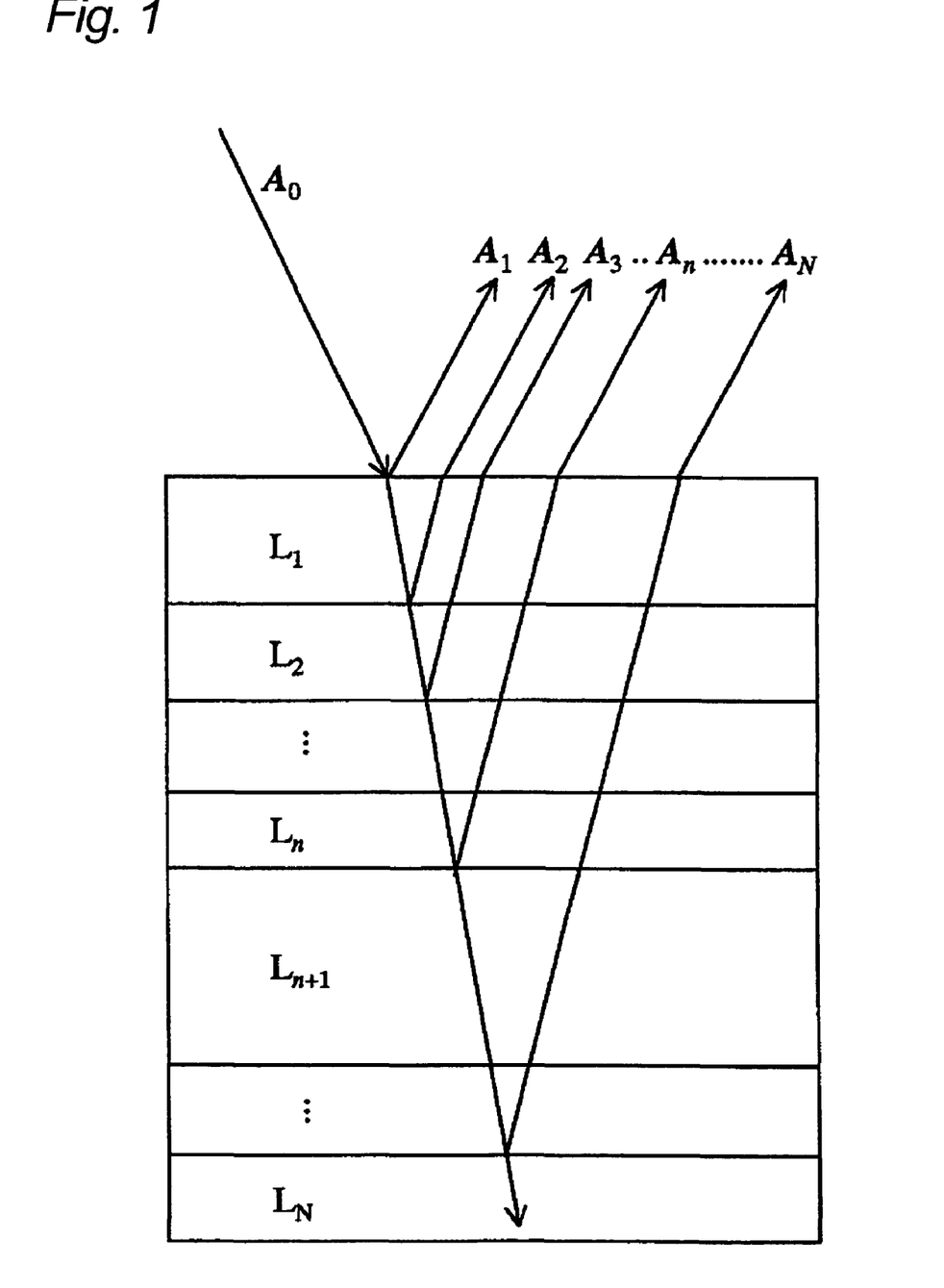
FIG. 1 is a diagram of reflecting light in a semiconductor multiple layer film consisting of N layers.

First, a process is explained for evaluating the internal electric field strength and thickness at the same time based on Franz-Keldysh oscillations of a semiconductor multiple layer film. FIG. 1 shows the reflected light from a semiconductor multiple layer structure consisting of N layers, where $A_0$ is incident light, and $A_n$ ($n \neq 0$) is light reflected from an interface between n-th layer $L_n$ and (n+1)-th layer $L_{n+1}$, where n is a natural number between 0 and N. The complex amplitude reflectance r of such a multiple layer structure is represented as follows.

$$r = r_0 + (1 - R_0) \sum_{n=1}^{N} C_n r_{n,n+1} e^{i\delta_n}, \quad (1)$$

where $r_0$ is complex amplitude reflectance and $R_0$ ($\equiv |r_0|^2$) is energy reflectance at the surface of the multiple layer structure, $r_{n,n+1}$ is complex amplitude reflectance at $L_n/L_{n+1}$ interface, and $C_n$ is a proportion constant related to transmittance. In Eq. (1), $\delta_n$ represents a quantity called as phase delay, given as follows.

$$\delta_n = \sum_{j=1}^{n} 2 k_j d_j \cos\theta_j, \quad (2)$$

where j is a natural number, and $k_j$ and $d_j$ are wave number of light and thickness of j-th layer in the multiple layer structure, respectively. Further, $\theta_j$ is reflection angle at the j-th layer, and it can be calculated based on the incident angle to the sample and the known index of refraction of the sample.

The energy reflectance R of the entire semiconductor multiple layer structure is given by a square $|r|^2$ of absolute value of the complex amplitude reflectance.

$$R \equiv r r^* \approx R_0 + 2(1 - R_0) \sum_{n=1}^{N} C_n \text{Re}[r_0 r_n] e^{i\delta_n}. \quad (3)$$

A relationship that $|r|^2 = r \cdot r^*$ is used here where $r^*$ is a complex conjugate of r. Further, it is assumed that the complex amplitude reflectance at the surface of the multiple layer structure is sufficiently larger than those at the interfaces therein. In a visible light region, $r_0$ can be taken generally as a real number. Then, the modulated reflectance $\Delta R_n$ at interface $L_n/L_{n+1}$ between the n-th layer $L_n$ and the (n+1)-th layer $L_{n+1}$ is represented as follows.

$$\Delta R_n = 2 r_0 (1 - R_0) C_n \text{Re}[\Delta r_{n,n+1} e^{i\delta_n}]. \quad (4)$$

In Eq. (4), $\Delta r_{n,n+1}$ is proportional to modulated component $\delta \in^{PR}_{n+1}$ of dielectric function. That is, $$\Delta r_{n,n+1} = B_n \delta \in^{PR}_{n+1}, \quad (5)$$

where $B_n$ is a proportion constant. In the case where $\delta_n \to 0$, that is, for a bulk crystal having no overlayers except the surface, Eq. (4) follows Eq. (6) on PR signals derived by Serafin et al.

$$\Delta R/R = \alpha \text{Re}[\delta \in^{PR}] + \beta \text{Im}[\delta \in^{PR}]. \quad (6)$$

Eq. (6) shows that the real and imaginary parts of the proportion constant $B_n$ in Eq. (4) correspond to Serafin coefficients α and β. In the visible light region, α is generally much larger than β. Therefore, $B_n$ can also be approximated as a real number. As a result, Eq. (4) is expressed as follows.

$$\Delta R_n \propto Re[\delta\varepsilon_{n+1}^{PR} e^{i\delta_n}]. \tag{7}$$

$$\delta\varepsilon_n^{PR}(\hbar\omega) \equiv \varepsilon_n^{on} - \varepsilon_n^{off} \tag{8a}$$
$$= -2ik_n \int_0^{W_n - \Delta W_n} e^{2ik_n z} \Delta\varepsilon_n(\hbar\omega, F_n^{on}(z)) dz +$$
$$2ik_n \int_0^{W_n} e^{2ik_n z} \Delta\varepsilon_n(\hbar\omega, F_n^{off}(z)) dz,$$

and $$\Delta\varepsilon_n(\hbar\omega, F_n) = \varepsilon_n(\hbar\omega, F_n) - \varepsilon_n(\hbar\omega, 0), \tag{8b}$$

where $\in_n(h\omega/2\pi, F_n)$ is a dielectric function perturbed by electric field $F_n$, where h is Planck constant, $\hbar$ is $h/2\pi$ and $(h\omega/2\pi)$ represents photon energy. $F_n^{on}(z)$ and $F_n^{off}(z)$ are strengths of electric field under the irradiation of pumping light and under no irradiation, respectively, and they are given as follows.

$$F_n^{off}(z) = F_n(z) \equiv \frac{F_{0,n}}{W_n}(W_n - z) \tag{9a}$$

and $$F_n^{on}(z) = \frac{F_{0,n}}{W_n}(W_n - \Delta W_n - z) = F_n(z + \Delta W_n), \tag{9b}$$

where $W_n$ is thickness of a depletion layer, $\Delta W_n$ is change in $W_n$ due to carriers generated by the irradiation of pumping light, and $F_{0,n}$ represents electric field strength at the interface when not irradiated with the pumping light.

Then, it is apparent that $W_n$ and $\Delta W_n$ have a following relationship with $F_n$ and $\Delta F_n$.

$$\Delta W_n / W_n = \Delta F_n / F_{0,n}. \tag{10}$$

If it is assumed that $\Delta E_n << F_{0,n}$ and $k_n \Delta W_n << 1$, Eq. (8a) is represented as follows.

$$\delta\varepsilon_n^{PR}(\hbar\omega) \approx 2ik_n \int_0^{W_n} \Phi_n(z) dz - \tag{11a}$$
$$2ik_n \left\{ \int_0^{W_n} \Phi_n(z + \Delta W_n) dz - \Phi_n(W_n + \Delta W_n) \Delta W_n \right\}$$

where $$\Phi_n(z) \equiv e^{2ik_n z} \Delta\in_n(\hbar\omega, F_n(z)). \tag{11b}$$

Further, by approximating $$\Phi_n(z + \Delta W_n) - \Phi_n(z) = (d\Phi_n(z)/dz) \Delta W_n,$$

and by neglecting terms higher than $(\Delta W_n)^2$, $\delta\in_n^{PR}$ is represented as follows.

$$\delta\in_n^{PR}(\hbar\omega) = 2ik_n \Delta\in_n(\hbar\omega, F_{0,n}) \Delta W_n \tag{12}$$

At $M_o$ singularity, $\Delta\in(h\omega/2\pi, F)$ is is represented as follows.

$$\Delta\varepsilon(\hbar\omega, F) \propto \frac{(\hbar\Theta)^{1/2}}{(\hbar\omega)^2} (g(-\eta) + if(-\eta)), \tag{13a}$$

where $$\eta \equiv \frac{\hbar\omega - E_0}{\hbar\Theta}. \tag{13b}$$

In Eq. (13a), g(-η) and f(-η) are functions called as electro-optic functions, and asymptotic solutions thereof at higher energy region above the band gap energy are represented as follows.

$$\hat{g}(-\eta) = \frac{1}{4}\eta^{-1}\sin\left(\frac{4}{3}\eta^{3/2}\right), \tag{14a}$$

and $$\hat{f}(-\eta) \approx -\frac{1}{4}\eta^{-1}\cos\left(\frac{4}{3}\eta^{3/2}\right). \tag{14b}$$

It is assumed here that the effect of the life time of electrons/holes on the electro-optic function can be neglected.

By using the asymptotic solutions, $\Delta R_n(h\omega/2\pi)$ or Franz-Keldysh oscillations are represented as follows.

$$\Delta R_n(\hbar\omega) \propto \frac{1}{4}\left(\frac{\hbar\omega - E_{0,n+1}}{\hbar\Theta_{n+1}}\right)^{-1}\cos\left(\frac{4}{3}\left(\frac{\hbar\omega - E_{0,n+1}}{\hbar\Theta_{n+1}}\right)^{3/2} + \delta_n\right), \tag{15}$$

where $E_{o,n+1}$ is band gap energy of (n+1)-th layer. Further, $(h/2\pi)\Theta_{n+1}$ is a physical quantity called as electro-optic energy, and it is represented by a following Equation.

$$(\hbar\Theta_{n+1})^3 \equiv \frac{e^2\hbar^2 F_{n+1}^2}{2\mu_{n+1}}, \tag{16}$$

where e and $\mu_{n+1}$ are elementary charge and reduced mass of electron and hole, respectively.

Figure 2:
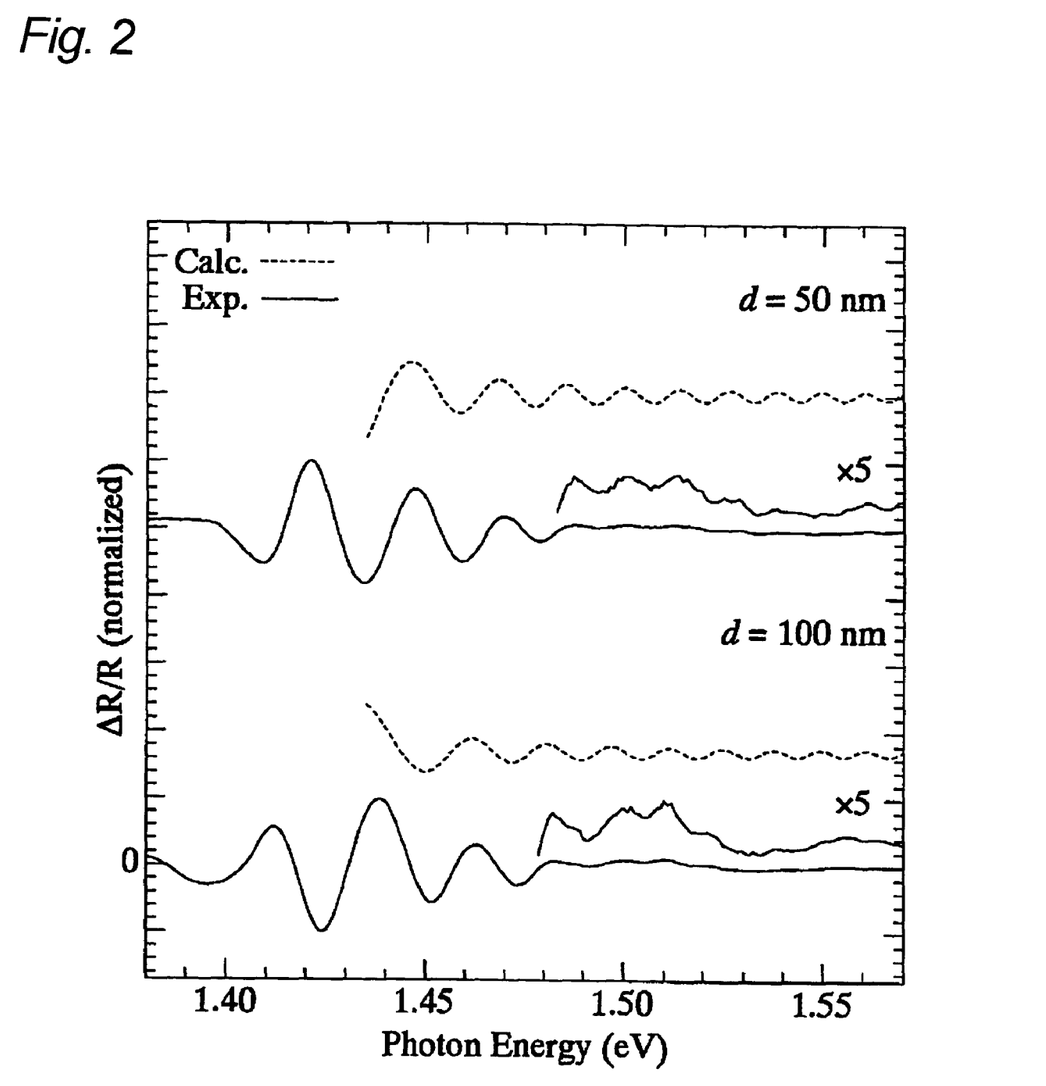
FIG. 2 is a graph of Franz-Keldysh oscillations of a heterojunction structure of $Al_{0.3}Ga_{0.7}As$ (thickness d nm)/GaAs.

FIG. 2 shows spectra (solid line) of Franz-Keldysh oscillations measured on a two-layer sample with $Al_{0.3}Ga_{0.7}As$ (having thickness of d nm)/GaAs heterojunction structure and another spectra (dashed line) of Franz-Keldysh oscillations obtained with numerical calculation with Eq. (15). The Franz-Keldysh oscillations shown in FIG. 2 are normalized. In FIG. 2, "×5" means data displayed with a scale of five times on the axis of ordinates. By comparing the solid and dashed lines, it is apparent that the phase of the Franz-Keldysh oscillations obtained by the numerical calculation agrees with that obtained experimentally though many approximations and assumptions are involved in the calculation. Therefore, the photon energies, at which Franz-Keldysh oscillations have maxima or minima, agree with the counterparts at which Eq. (15) has maxima or minima. In Eq. (15), the photon energy of the m-th extremum of the Franz-Keldysh oscillations from the band gap energy $E_{0,n}$ follows Eq. (17).

$$\frac{4}{3\pi}(E_m - E_{0,n})^{3/2} = (\hbar\Theta_{n+1})^3(m - \delta_n/\pi). \qquad (17)$$

The plot of the extrema of the Franz-Keldysh oscillations according to Eq. (17) has a linear form. Then, the slope of the line gives the electro-optic energy $(h/2\pi)\Theta_{n+1}$, and the electric field strength $F_{0,n+1}$ can be calculated from this value based on Eq. (16). On the other hand, an intercept at the axis of ordinates gives phase delay $\delta_n$. The phase delay is determined by performing this plot for the Franz-Keldysh oscillations arising from each interface. According to the definition of $\delta_n$ (Eq. (2)), a difference between $\delta_n$ and $\delta_{n-1}$ has a following relationship.

$$\delta_n - \delta_{n-1} = 2k_n d_n \cos\Theta_n. \qquad (18)$$

The thickness $d_n$ of n-th layer can be derived from this Equation. Thus, the internal electric field strength and the thickness in the layers of a semiconductor multiple layer structure can be evaluated at the same time from the Franz-Keldysh oscillations.

It is known that the electric field strength can be obtained from the electro-optic energy by plotting the extrema of the Franz-Keldysh oscillations; however, the physical background on the intercept was not understood. The plot proposed here has a characteristic that the phase delay is obtained from the intercept at the axis of ordinates and that the thickness is obtained therefrom.

Figure 3:
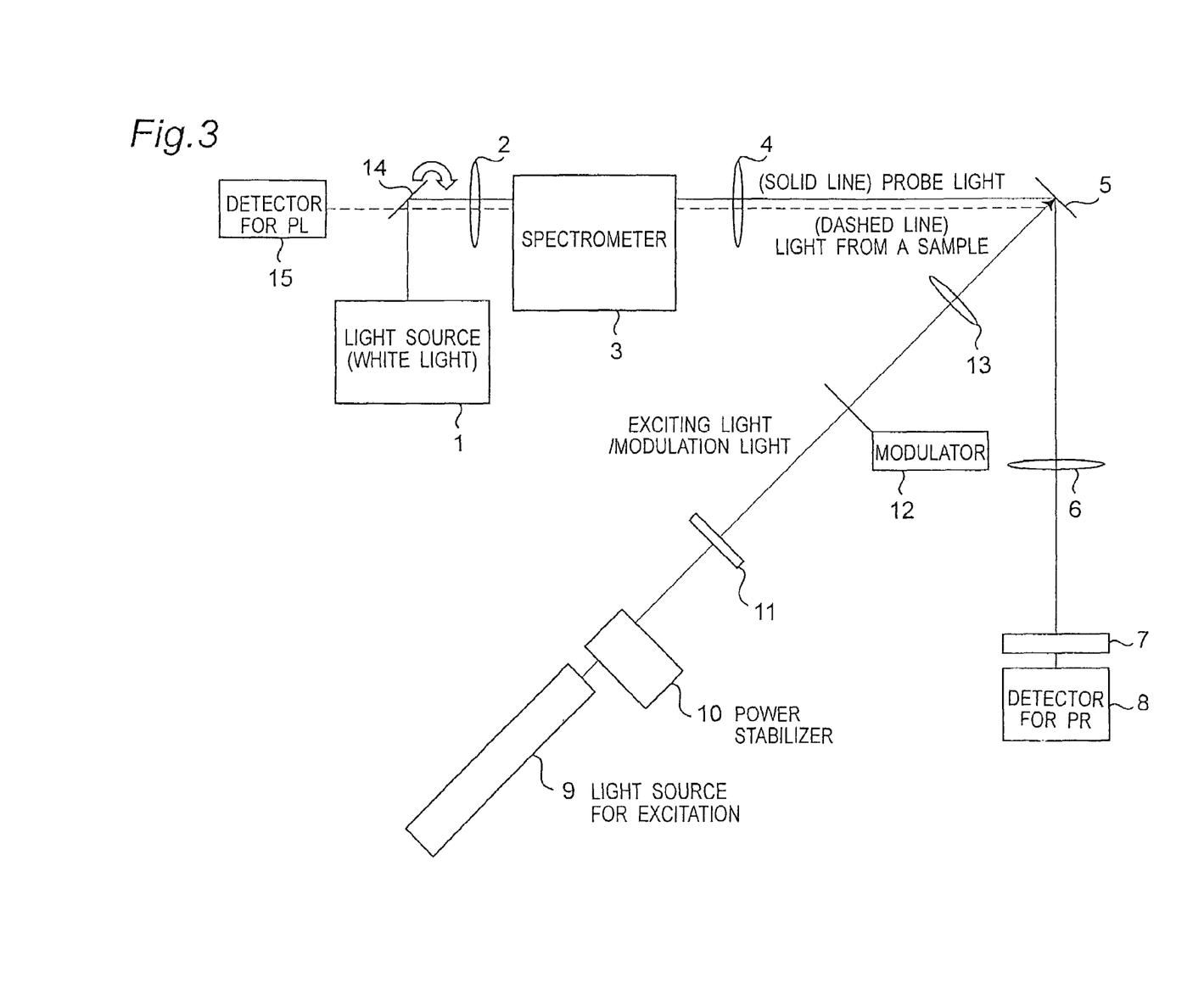
FIG. 3 is a diagram of an optical measurement system in a PL/PR measuring apparatus.
Figure 4:
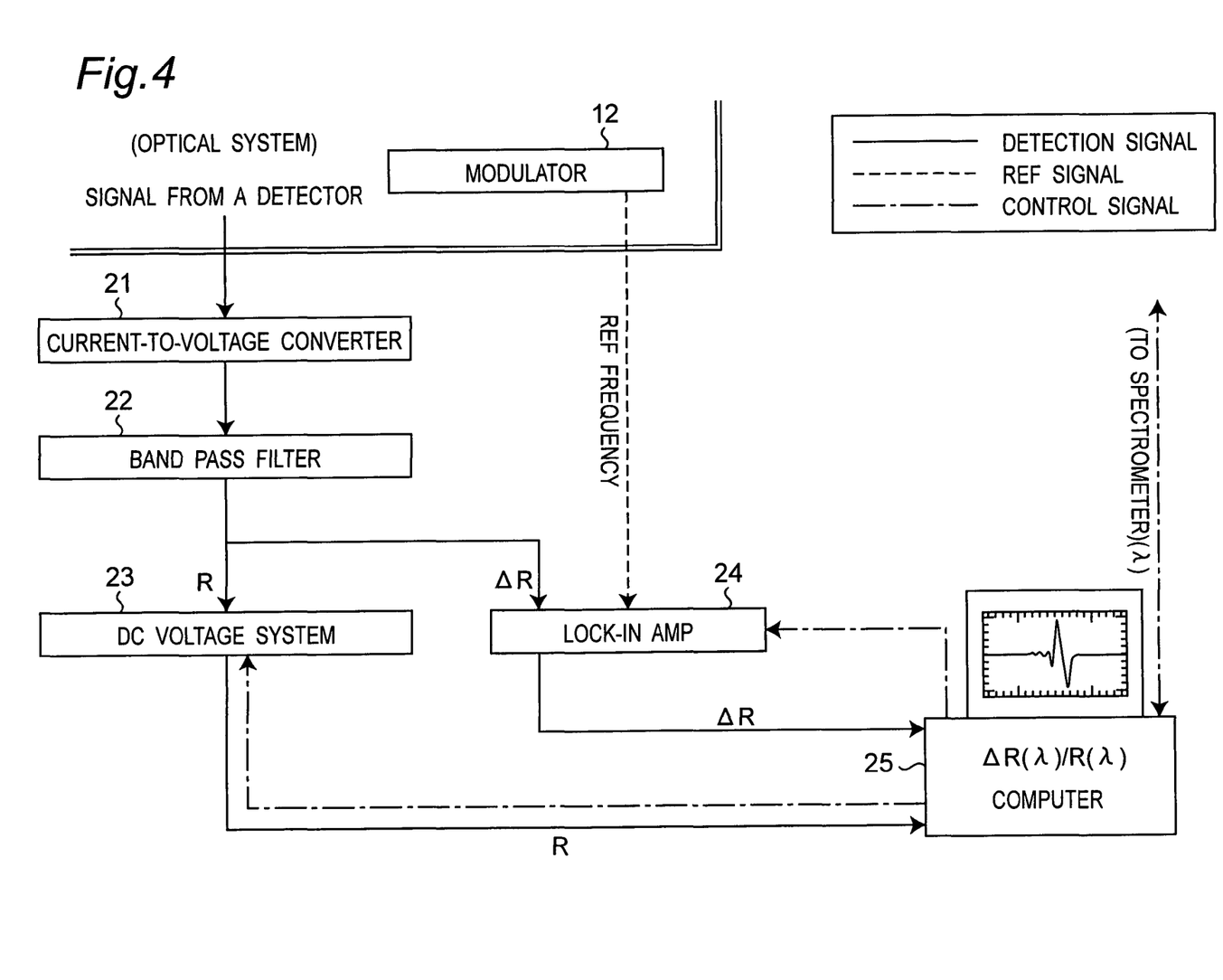
FIG. 4 is a diagram of a signal processing system in the PL/PR measuring apparatus.

FIGS. 3 and 4 show an apparatus to measure PR and PL spectra based on the above-mentioned principle. FIG. 3 schematically shows an optical measuring system, and FIG. 4 shows a signal processing system in the apparatus. In the signal processing system shown in FIG. 4, PR and PL signals detected by the optical measuring system are processed.

As shown in FIG. 3, an optical path is changed with a mirror 14 in order to measure PR or PL spectra. In each case of the measurement of PR or PL spectra, the measurement data obtained by the optical measuring system is processed by the signal processing system shown in FIG. 4.

In the optical system provided in the measuring apparatus, a light source 1 of white light is used to provide probe light, and it is, for example, a lamp. When PR spectra are measured, the mirror 14 reflects the light from the light source 1 toward a spectrometer 3. A condenser lens 2 guides the light to the spectrometer 3 in order to generate the probe light. The spectrometer 3 generates monochromatic light from the lamp light and supplies the probe light to detect the reflectance R and modulated reflectance $\Delta R$. The condenser lens 4 focuses the probe light generated by the spectrometer 3 onto the surface of a sample 5.

Further, a light source 9 for excitation light, such as a laser device, generates the external modulated light when PR spectra are measured. A power stabilizer 10 stabilizes the power of the light source 9. A filter 11 for the light source such as a neutral density filter is provided for controlling the intensity of the excitation light. A modulator 12 such as an optical chopper converts the continuous wave form of the light to a square wave form. A condenser lens 13 focuses the external modulated light onto a region irradiated with the probe light in a surface of the sample.

The excitation light source 9 such as a laser device generates the excitation light for PL spectrum measurement and/or the external modulated light for PR spectrum measurement. The spectrometer 3 generates the monochromatic light used as the probe light from the light emitted by the light source 1 in order to detect reflectance R and modulated reflectance $\Delta R$. Further, the spectrometer 3 is used to disperse the light from a sample when PL spectra are measured.

The condenser lens 6 guides the probe light reflected from the sample 5 to a detector 8 for PR measurement. A long path filter 7 removes the external modulated light scattered at the sample 5. The detector 8 converts the light signals reflected from the sample 5 to electrical signals.

When PL spectra are measured, the light source 9 generates excitation light for the sample 5. The lens 4 condenses the light emitted from the sample 5, as shown with dashed line, to the spectrometer 3. The spectrometer 3 disperses the light emitted from the sample 5, and the condenser lens 2 sends the photoluminescence to a detector 15. At this time, the direction of the mirror 14 is changed so that the as-received photoluminescence is sent to the detector 15.

FIG. 4 schematically shows the signal processor for signals detected by the measuring system shown in FIG. 3. In the signal processor, a current-to-voltage converter 21 converts a current signal received from the detector 8 or 15 to a voltage signal. A band-path filter 22 is a frequency filter for separating the ac (corresponding to $\Delta R$) and dc signals (signal R) from the overall signal. A dc voltmeter 23 is a device for measuring the dc component. A lock-in amplifier 24 is a device used for phase detection of the ac components or lock-in detection. A reference frequency signal for the lock-in amplifier 24 is provided from a modulator 12 of the optical measuring system. When the pumping light is intermittent light, the signal from the detector 15 is measured by the lock-in amplifier, while when it is a continuous light, the signal is measured by the dc voltmeter 23. A computer 25 controls the above-mentioned components for the measurement, acquires all the signals, and calculates on the basis of the acquired signals. The computer 25 controls the spectrometer 3 and records input signals from the dc voltmeter 23 or the lock-in amplifier 24. For example, for the modulated reflection spectra, the change in reflectance $\Delta R/R$ is calculated and recorded based on the signals from the detector 15 as a function of photon energy $(h\omega/2\pi)$. Thus, the change in reflectance $\Delta R/R$ can be recorded as a function of photon energy $(h\omega/2\pi)$. Then, by deriving and plotting the above-mentioned Franz-Keldysh oscillations of the semiconductor multiple layer structure, the internal electric field strength and the thickness are evaluated simultaneously based on the Franz-Keldysh oscillations.

Next, steps for a measurement with the spectrum measuring apparatus is explained.

(A) In order to measure PL spectra of an epitaxial wafer (sample 5), the direction of the mirror 14 is changed so that the light from the sample 5 enters the detector 15. When the PL spectra are measured, it is desirable to deactivate the unnecessary light source 1 of white light.

(B) The excitation light such as laser light irradiates the sample 5. The excitation light may be intermittent light generated by the modulator 12 or continuous light without using the modulator 12. However, if the light from the sample is very weak, in order to improve signal-to-noise ratio, the combination of the modulator 12 and the lock-in amplifier 24 is used, where the lock-in amplifier 24 is used to detect the light in synchronization with the phase of the intermittent light. In this case, the phase of the lock-in amplifier is matched with that of the intermittent light as follows. First, the excitation light scattered by the sample 5 is collected by the condenser lens 4 to the spectrometer 3. Then, the detector 15 detects the light transmitting the spectrometer 3, and the phase of the lock-in amplifier 24 is matched with the detected signal.

(C) The light from the sample 5 transmits through the lens 4 to a slit of the spectrometer 3.

(D) The light outgoing from the spectrometer 3 is focused by the lens 2 onto the detector 15 which converts the optical signal to an electrical signal.

(E) The signal obtained by the detector 15 is measured with the lock-in amplifier 24 when the pumping light is intermittent light, or with the dc voltmeter 23 when it is continuous light.

Figure 5:
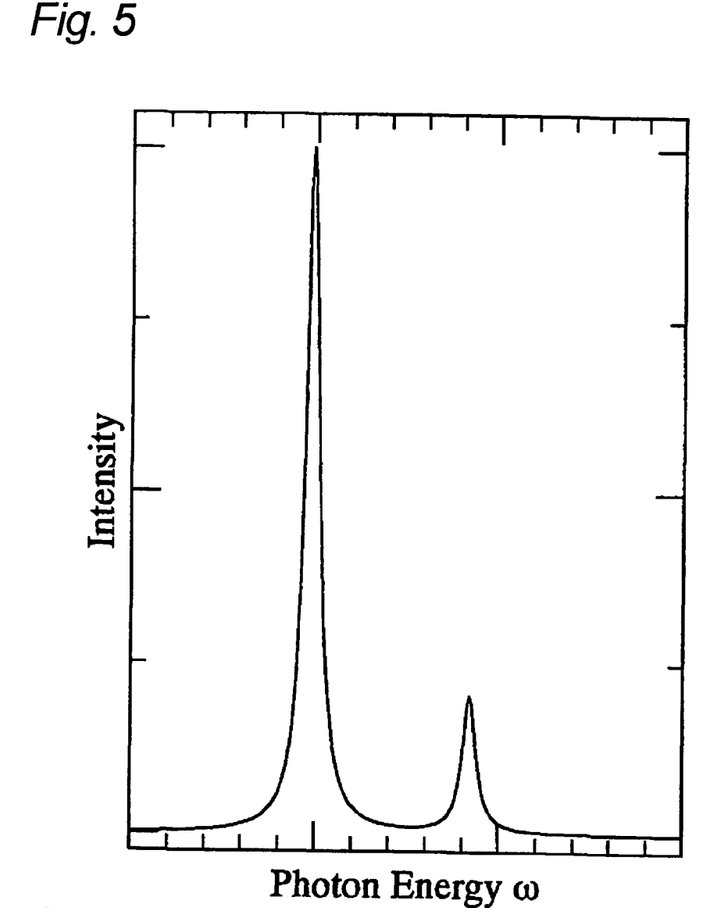
FIG. 5 is a graph of a typical PL spectrum observed with the optical measuring system shown in FIG. 3.

(F) Light intensity is recorded, by sweeping the spectrometer 3, as a function of wavelength $\lambda$ or photon energy ($h\omega/2\pi$) as shown in FIG. 5.

(G) The band gap energy is determined based on peaks of the observed photoluminescence spectra. The positions of the peaks correspond to band gap energy of each layer.

(H) Next, the direction of the mirror 14 is changed in order to measure PR spectra of the epitaxial wafer, so that the light of the white light source 1 (such as a lamp) enters the spectrometer 3. In this state, the light outgoing from the spectrometer 3 is probe light.

(I) External modulated light such as a laser beam from the light source 9 is irradiated onto the sample 5.

(J) By removing the long path filter 7, the external modulated light scattered by the sample 5 enters the detector 8. In this state, the phase of the lock-in amplifier 24 is matched with the detected signal as a reference signal.

(K) The long path filter 7 is inserted so that the external modulated light is prevented from entering the detector 8.

(L) The spectrometer 3 is swept, and the probe light is detected by the detector 8.

(M) The detected signal is transmitted through the band path filter 22 to separate the dc component corresponding to reflectance R from ac components corresponding to modulated reflectance $\Delta R$.

(N) The dc and ac components are measured with the dc voltmeter 23 and the lock-in amplifier 24, respectively.

(O) The computer 25 calculates $\Delta R/R$ to obtain PR signals.

(P) By repeating the above-mentioned steps K to O, the PR spectra $\Delta R/R$ is recorded as a function of wavelength $\lambda$ or photon energy ($h\omega/2\pi$).

Figure 6:
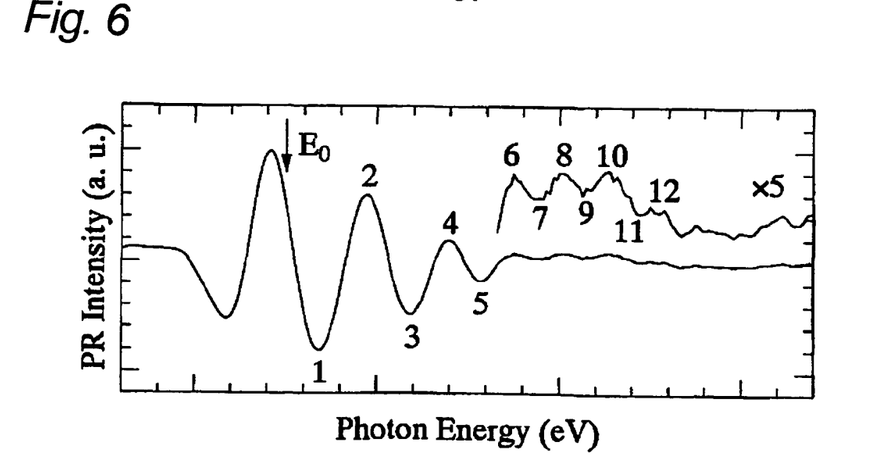
FIG. 6 is a graph of a typical PR spectrum observed with the optical measuring system shown in FIG. 3.

(Q) Numbering is performed on the extrema appearing in the Franz-Keldysh oscillations in the PR spectra, in the order from $E_0$ to higher energy, as shown in FIG. 6. The numbers (m=1, 2, 3, . . . ) shown in FIG. 6 represent indices for the extrema of the Franz-Keldysh oscillations in the photoreflectance (PR) spectrum, and an arrow shows the position of band gap energy $E_o$. It is noted in FIG. 6 that the scale of the axis of ordinates is displayed in five times for indices equal to or larger than 6.

Figure 7:
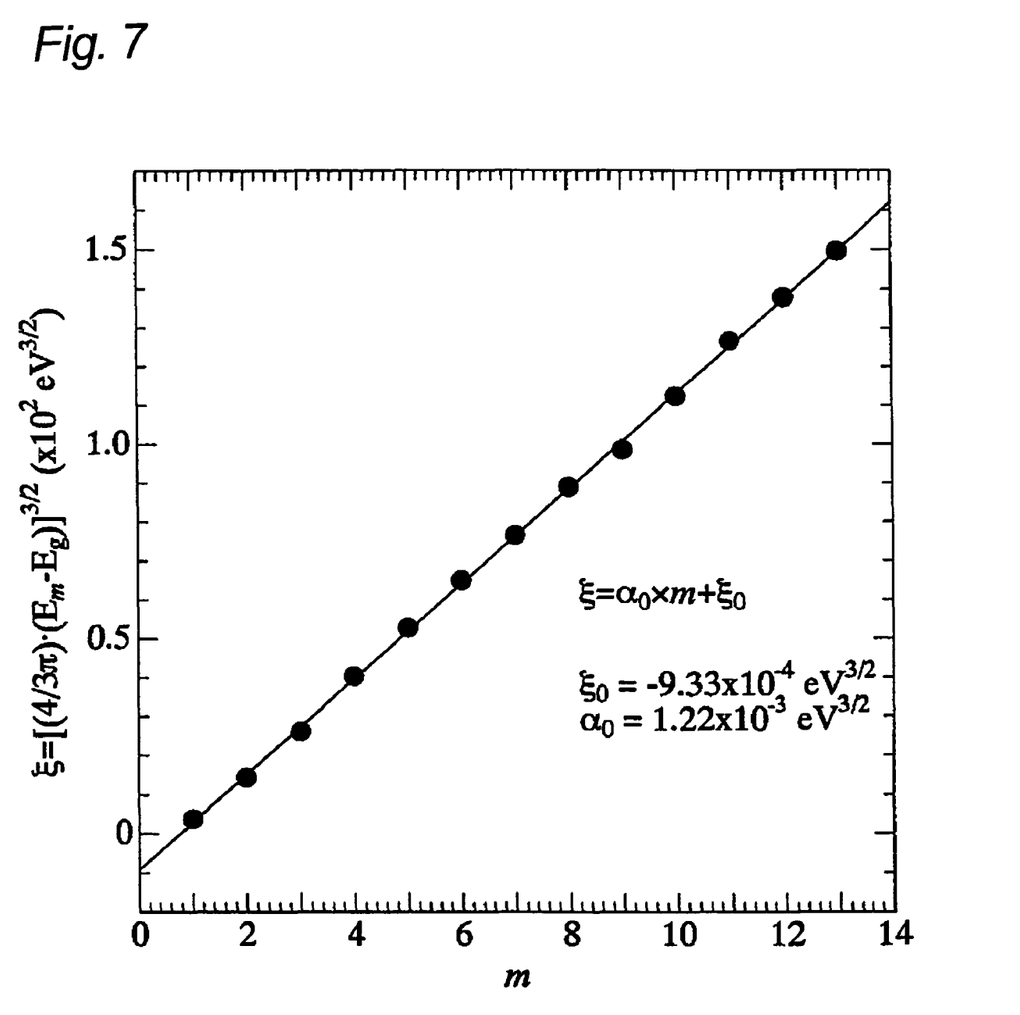
FIG. 7 is a graph of the plot of the extremum positions of energy of Franz-Keldysh oscillations as a function of its index.

(R) The obtained extrema are plotted according to Eq. (17). As shown in an example in FIG. 7, $\xi$ is proportional to index m.

(S) Fitting is performed with parameters $(h/2\pi)\Theta_n$ and $\delta_n$ in Eq. (17).

(T) The electric field strength is obtained from $(h/2\pi)\Theta_n$ according to Eq. (16), and the thickness is determined from $\delta_n$ according to Eq. (18).

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A measuring apparatus for characterizing a semiconductor multiple layer film comprising:
   a first light source which generates light for exciting a sample including a semiconductor multiple layer film for measurement of a photoluminescence spectrum of the sample and generates externally modulated light for measurement of a reflection spectrum of the sample;
   a second light source which generates white light as probe light for measuring the reflection spectrum;
   a spectrometer which disperses light emitted by the sample for the measurement of the photoluminescence spectrum and disperses the light from said second light source to irradiate the sample for the measurement of the reflection spectrum;
   a first detector for the measurement of the photoluminescence spectrum, detecting light emitted from said spectrometer and converting the light detected to an electrical signal;
   a second detector for the measurement of the reflection spectrum, detecting light dispersed by said spectrometer, irradiating the sample, and reflected from the sample;
   a guide member which selectively guides the white light from said second light source to said spectrometer and permits passage of light emitted from said spectrometer to said first detector; and
   a controller which makes said guide member guide the white light from said second light source to said spectrometer, acquires electrical signals from said second detector for the measurement of the reflection spectrum, makes said guide member pass the light emitted from said spectrometer to said first detector, and acquires electrical signals from said first detector for the measurement of the photoluminescence spectrum.

2. The apparatus according to claim 1, wherein said controller further records photon energy dependence of modulated reflectance based on electrical signals from the second detector.

3. The apparatus according to claim 1, wherein said first light source further comprises a modulator which converts light into periodic intermittent light, and said apparatus comprises a lock-in amplifier which amplifies an electrical signal from said first or second detectors according to phase of the intermittent light.

4. A measuring method for characterizing a semiconductor multiple layer structure comprising:
   irradiating a sample including a semiconductor multiple layer structure with excitation light;
   detecting photoluminescence from the sample as a function of wavelength with a spectrometer, and recording detected light intensity as a function of wavelength;
   supplying white light to the spectrometer and irradiating the sample with monochromatic light emitted from the spectrometer; and
   changing wavelength of the monochromatic light emitted from the spectrometer while irradiating the sample with the monochromatic light and externally modulated light, detecting light reflected from the sample, and recording a detected reflection spectrum as a function of wavelength from the light reflected and detected.

5. The method according to claim 4, further comprising:
calculating wavelength dependence of reflectance based on the detected reflection spectrum; and
determining electric field strength F and thickness δ from extrema of an oscillation pattern of the wavelength dependence according to:

$$\frac{4}{3\pi}(E_m - E_{0,n})^{3/2} = \left(\frac{e^2 \hbar^2 F_{n+1}^2}{2\mu_{n+1}}\right)(m - \delta_n/\pi),$$

where m and n are natural numbers, $E_m$ is energy of m-th extremum of the oscillation pattern, $E_{0,n}$ is band gap energy of n-th layer in the semiconductor multiple layer structure, $F_n$ is electric field in the n-th layer, e is elementary charge, $\mu_n$ is reduced mass of electrons and holes in the n-th layer, and $\delta_n$ represents a quantity given by $$\delta_n = \sum_{j=1}^{n} 2k_j d_j \cos\theta_j$$

where j is a natural number, $k_j$ and $d_j$ are wave number of light and thickness in j-th layer in the semiconductor multiple layer structure, respectively, and $\theta_j$ is angle of refraction in the j-th layer.

* * * * *